(12) United States Patent
Baron et al.

(10) Patent No.: US 7,175,897 B2
(45) Date of Patent: Feb. 13, 2007

(54) ADHESIVE ARTICLES WHICH CONTAIN AT LEAST ONE HYDROPHILIC OR HYDROPHOBIC LAYER, METHOD FOR MAKING AND USES FOR SAME

(75) Inventors: Richard Baron, Painesville, OH (US); Paul Boulier, Concord Township, OH (US); Michael Gilbert, Lansdale, PA (US); Thanh V. Nguyen, Painesville, OH (US); Frank Rizzo, Perry, OH (US); Frank Y. Shih, Arcadia, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/712,978

(22) Filed: Nov. 12, 2003

(65) Prior Publication Data

US 2004/0115412 A1    Jun. 17, 2004

(51) Int. Cl.
*B32B 1/02* (2006.01)
(52) U.S. Cl. .................. 428/36.91; 428/343; 72/836; 436/52
(58) Field of Classification Search ............... 214/403; 428/411.1, 483, 520, 522, 36.91, 343; 72/836; 436/52
See application file for complete search history.

(56) References Cited

U.S. PATENT DOCUMENTS

| | | | |
|---|---|---|---|
| 4,539,996 A | 9/1985 | Engel | 128/640 |
| 4,545,382 A | 10/1985 | Higgins et al. | 128/635 |
| 4,675,009 A | 6/1987 | Hymes et al. | 604/304 |
| 4,711,245 A | 12/1987 | Higgins et al. | 128/635 |
| 4,757,022 A | 7/1988 | Shults et al. | 435/291 |
| 4,891,319 A | 1/1990 | Roser | 435/188 |
| 5,053,199 A | 10/1991 | Keiser et al. | 422/68.1 |
| 5,120,420 A | 6/1992 | Nankai et al. | 204/403 |
| 5,262,035 A | 11/1993 | Gregg et al. | 204/403 |

(Continued)

FOREIGN PATENT DOCUMENTS

JP        2001-031907        *   2/2001

OTHER PUBLICATIONS

Derwent Document No. 1983-848572 (RD-23619A)., 1983.*

(Continued)

*Primary Examiner*—D. Lawrence Tarazano
(74) *Attorney, Agent, or Firm*—Renner, Otto, Boisselle & Sklar, LLP

(57) ABSTRACT

The present invention relates to an adhesive article which can be used as a layer in or a cover for various articles in which a hydrophilic or hydrophobic surface is desired. The adhesive article includes a base layer having a first surface and a second surface and a coating layer formed on the first surface of the base layer, where the coating layer contains at least one adhesive resin and at least one hydrophilic polymer; at least one adhesive resin (which can be a hydrophobic polymer) and at least one surfactant; or at least one adhesive resin, at least one hydrophilic polymer and at least one surfactant. Given the application, the coating layer can be formulated to provide either a hydrophilic or hydrophobic surface. The polymer portion of the coating provides the coating layer with sufficient hydrophilic properties to increase the rate fluid transport across (or in the area near) the coating layer.

22 Claims, 1 Drawing Sheet

U.S. PATENT DOCUMENTS

| | | | |
|---|---|---|---|
| 5,278,217 A | 1/1994 | Umeda et al. | 524/394 |
| 5,288,636 A | 2/1994 | Pollmann et al. | 435/288 |
| 5,320,732 A | 6/1994 | Nankai et al. | 204/403 |
| 5,364,678 A | 11/1994 | Lumb et al. | 428/96 |
| 5,366,609 A | 11/1994 | White et al. | 204/403 |
| 5,382,346 A | 1/1995 | Uenoyama et al. | 204/403 |
| D369,216 S | 4/1996 | Micinski et al. | D24/169 |
| 5,508,171 A | 4/1996 | Walling et al. | 205/777.5 |
| 5,509,410 A | 4/1996 | Hill et al. | 128/637 |
| 5,575,403 A | 11/1996 | Charlton et al. | 221/31 |
| 5,593,852 A | 1/1997 | Heller et al. | 435/14 |
| 5,620,579 A | 4/1997 | Genshaw et al. | 204/402 |
| 5,627,075 A | 5/1997 | Bateson | 436/8 |
| 5,628,890 A | 5/1997 | Carter et al. | 204/403 |
| 5,629,370 A * | 5/1997 | Freidzon | 524/503 |
| 5,670,097 A | 9/1997 | Duan et al. | 264/1.24 |
| 5,682,884 A | 11/1997 | Hill et al. | 128/637 |
| 5,688,855 A | 11/1997 | Stoy et al. | 524/505 |
| 5,708,247 A | 1/1998 | McAleer et al. | 204/403 |
| 5,723,284 A | 3/1998 | Ye | 435/4 |
| 5,727,548 A | 3/1998 | Hill et al. | 128/637 |
| 5,738,244 A | 4/1998 | Charlton et al. | 221/26 |
| 5,759,364 A | 6/1998 | Charlton et al. | 204/403 |
| 5,780,148 A | 7/1998 | Ohtake et al. | 428/333 |
| 5,783,056 A | 7/1998 | Hampp et al. | 204/403 |
| 5,807,917 A | 9/1998 | Sulc et al. | 524/377 |
| 5,820,551 A | 10/1998 | Hill et al. | 600/347 |
| 5,916,156 A | 6/1999 | Hildenbrand et al. | 600/347 |
| RE36,268 E | 8/1999 | Szuminsky et al. | 205/777.5 |
| 5,936,020 A * | 8/1999 | Freidzon | 524/377 |
| 5,957,889 A | 9/1999 | Poulsen et al. | 604/131 |
| 5,958,199 A | 9/1999 | Miyamoto et al. | 204/403 |
| 5,961,496 A | 10/1999 | Nielsen et al. | 604/209 |
| 5,997,817 A | 12/1999 | Crismore et al. | 422/58 |
| 6,001,916 A * | 12/1999 | Walker et al. | 524/459 |
| 6,042,931 A * | 3/2000 | Laprade | 428/202 |
| 6,045,537 A | 4/2000 | Klitmose | 604/224 |
| 6,045,567 A | 4/2000 | Taylor et al. | 606/181 |
| 6,051,748 A | 4/2000 | Auguste et al. | 602/54 |
| D428,150 S | 7/2000 | Ruf et al. | D24/146 |
| 6,129,823 A | 10/2000 | Hughes et al. | 204/409 |
| RE36,991 E | 12/2000 | Yamamoto et al. | 204/403 |
| 6,156,051 A | 12/2000 | Schraga | 606/181 |
| 6,197,040 B1 | 3/2001 | LeVaughn et al. | 606/182 |
| 6,207,000 B1 | 3/2001 | Schwobel et al. | 156/248 |
| 6,241,862 B1 | 6/2001 | McAleer et al. | 204/403 |
| 6,245,851 B1 * | 6/2001 | Petrocelli et al. | 524/459 |
| 6,248,090 B1 | 6/2001 | Jensen et al. | 604/67 |
| 6,254,736 B1 | 7/2001 | Earl et al. | 204/164 |
| 6,258,229 B1 | 7/2001 | Winarta et al. | 204/403 |
| 6,277,098 B1 | 8/2001 | Klitmose et al. | 604/207 |
| 6,284,125 B1 | 9/2001 | Hodges et al. | 205/775 |
| 6,284,365 B1 | 9/2001 | Hirose et al. | 428/333 |
| 6,291,050 B1 | 9/2001 | Cree et al. | 428/131 |
| 6,302,855 B1 | 10/2001 | Lav et al. | 600/584 |
| 6,309,723 B1 | 10/2001 | Ding et al. | 428/36.92 |
| 6,348,212 B2 | 2/2002 | Hymes et al. | 424/449 |
| 6,420,622 B1 | 7/2002 | Johnston et al. | 602/41 |
| 6,455,065 B1 | 9/2002 | Hymes | 424/449 |
| 6,479,015 B1 | 11/2002 | Long et al. | 422/58 |
| 6,511,927 B1 | 1/2003 | Ellis et al. | 442/77 |
| 2002/0115974 A1 | 8/2002 | Hermansson et al. | 604/385.01 |
| 2002/0173211 A1 | 11/2002 | Kocinec et al. | 442/286 |

OTHER PUBLICATIONS

International Search Report, Application No. PCT/US03/38167, mailed Oct. 28, 2005.

RD 23601A (Derwent Document No. 1983-84872); Dec. 10, 1983.

* cited by examiner

ADHESIVE ARTICLES WHICH CONTAIN AT LEAST ONE HYDROPHILIC OR HYDROPHOBIC LAYER, METHOD FOR MAKING AND USES FOR SAME

FIELD OF THE INVENTION

The present invention relates to an adhesive article which can be used as a layer in or a cover for various articles in which a hydrophilic or hydrophobic surface is desired. The adhesive article includes a base layer having a first surface and a second surface and a coating layer formed on the first surface of the base layer, where the coating layer contains at least one adhesive resin. The coating layer provides sufficient hydrophilic properties to improve fluid transport across (or in the area near) the coating layer.

BACKGROUND OF THE INVENTION

A variety of products utilize and/or rely upon a hydrophilic or hydrophobic material to increase fluid transport. For example, medical devices (e.g., medical diagnostic sensors, bandages, wound dressings, etc.), general chemical analyte sensors (e.g., water analysis sensors) or devices which are used in a wet and/or moist environment and function via capillary action often contain a hydrophilic material which has been deposited in or placed on at least a portion of the device/product in order to increase the fluid transfer properties thereof.

Generally, one problem that arises in such devices/products is that at least one extra production step must be used to place the hydrophilic or hydrophobic material in the desired place(s) in or near the portion of the device where increased hydrophilicity or hydrophobicity is desired. For example, in a closed capillary space used to transport fluid, the hydrophilic or hydrophobic material is generally deposited somewhere near the capillary opening or on a surface of the capillary space in order to facilitate better fluid transport.

The devices are often subjected to a desiccation step during the manufacture or during their transport. The desiccation removes the moisture from the hydrophilic materials. Moisture may interfere with the device's ability to give reliable and accurate test results. Hydrophilic materials often lose their ability to promote fluid transport.

Another problem that arises is that the hydrophilic or hydrophobic material needs to be stable so that the hydrophilic or hydrophobic material can offer fast and reliable transport of a variety of fluids across its surface, even after being stored for long periods of time (e.g., more than 3 months).

SUMMARY OF THE INVENTION

The present invention relates to an adhesive article comprising: a base layer having a first surface and a second surface; and a coating layer formed on the first surface of the base layer, wherein the coating layer comprises: (A) at least one adhesive resin and (B) at least one hydrophilic polymer, at least one surfactant or a combination of at least one hydrophilic polymer and at least one surfactant, with the proviso that when (B) is only a surfactant, then the coating layer contains less than about 40% by weight polyurethane. The coating layer can be formulated to improve fluid transport across (or in the area near) the coating layer. The coating composition maintains good hydrophilic characteristics even after desiccation. The adhesive articles provide an effective heat seal to promote fluid transport across or along the coating layer of the adhesive article. The coating layer of the adhesive articles of the present invention show good adhesive properties even though the coating layer contains one or more surfactants. The invention also relates to methods of making the adhesive articles and devices and substrates having a place for fluid transport and a covering or lid made by the adhesive articles. The adhesive articles are useful as lids for biosensor devices (e.g., glucose, cholesterol, etc.). These lids provide improved fluid transport even after desiccation.

DETAILED DESCRIPTION

Figure 1:
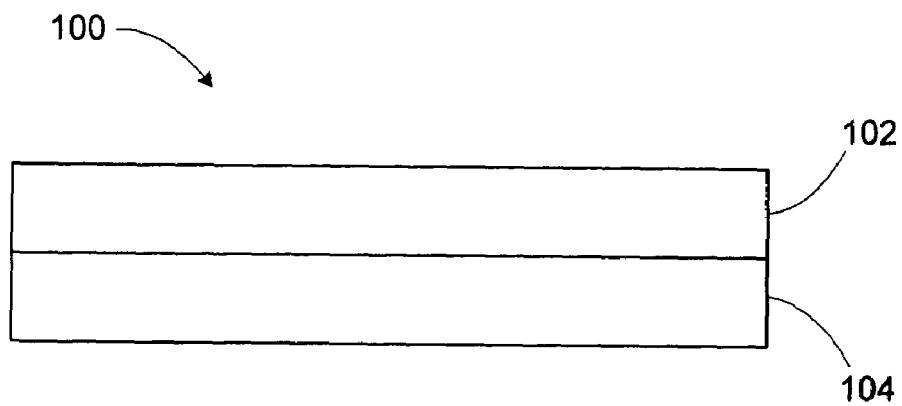
FIG. 1 is a cross-section view of an adhesive article, according to one embodiment of the present invention.

As discussed above, the present invention relates to an adhesive article which is a combination of a base layer and a coating layer. The base layer may be prepared from one or more layers of polymers. The base layer may be a multilayer film containing two or more layers which is prepared by extrusion (including co-extrusion) or laminating films together with adhesive or heat. The base layer may be embossed or not embossed. Typically, the base layer is not embossed.

Base Layer

The base layer is formed from a polymer film. The base layer generally has a thickness of about 0.1 mil to about 20 mils, or from about 0.5 mil to about 15 mils, or even from about 0.75 mil to about 10 mils.

In one embodiment, the polymer film from which the base layer formed is heat stabilized. The heat stabilization of polymer films is known in the art. One manner by which heat stabilization is achieved is by the use of a heated blow mold in the manufacture of a blown film. The use of a heated blow mold can raise the level of crystallinity in a polymer film and relax some of the stresses induced into a polymer film. The film has a reduced amount of shrinkage when exposed to elevated processing temperatures (e.g., above about 75° C., or above about 80° C., or even above about 85° C.).

The film may be oriented or non-oriented. In another embodiment, the polymer film from which the base layer is formed is optionally subjected to orientation. The base layer film may be either uniaxially or biaxially oriented. If the film is uniaxially oriented, such orientation can be in either the machine direction or the transverse direction.

Suitable polymer films for the base layer include, but are not limited to, polycarbonate polymer films, polyacryl polymer films, polymethacryl polymer films, styrenic polymer films, polyolefin polymer films or polyester polymer films or co-polymer films formed from one or more of the above-mentioned polymers.

In one embodiment, the base layer is formed from a polyolefin polymer. The polyolefins which can be utilized as the material from which the base layer is formed include, but are not limited to, polymers and copolymers of ethylene, propylene, 1-butene, hexene, octene, or blends or mixtures of such polymers and copolymers. In one embodiment, the polyolefins comprise polymers and copolymers of ethylene and propylene. In another embodiment, the polyolefins comprise propylene homopolymers, and copolymers, such as propylene-ethylene and propylene-1-butene copolymers. Blends of polypropylene and polyethylene with each other, or blends of either or both of them with polypropylene-polyethylene copolymer also are useful. In another embodiment, the polyolefin film materials are those with a very high propylenic content, either polypropylene homopolymer or propylene-ethylene copolymers or blends of polypropylene and polyethylene with low ethylene content, or propylene-1-butene copolymers or blends of polypropylene and poly-1-butene with low butene content.

Various polyethylenes can be utilized as the first polymer material including low, medium, and high density polyethylenes. An example of a useful low density polyethylene (LDPE) is Rexene 1017, available from Huntsman.

In another embodiment, useful polyolefins include very low density polyethylene (ULDPE), which has been referred to as ultra low density polyethylene, linear low density polyethylene (LLDPE), linear low density polyethylene (LLPE), etc. Very low density polyethylene (VLDPE) has a density of about 0.885–0.912 g/cc. Such VLDPE resins are commercially available from union Polymer Co.

In still another embodiment, the polymer utilized to form the base layer film is a polyolefin or a thermoplastic polymer of ethylene or propylene, or a mixture containing these polymers. In another embodiment, the polymer is polyethylene, polypropylene, thermoplastic polymers of ethylene or propylene.

In still another embodiment, the polymer from which the base layer is formed is an ethylene/alpha-olefin copolymer. These polymers generally designate copolymers of ethylene with one or more co-monomers, such as 1-butene, 1-pentene, 1-hexene, 1-octene, methyl pentene and the like, in which the polymer molecules comprise long chains with relatively few side chain branches. These polymers are obtained by low pressure polymerization processes and the side branching, which if present, will be short compared to non-linear polyethylenes (e.g., LDPE, a low density polyethylene homopolymer).

Ethylene/alpha-olefin copolymers generally have a density in the range of from about 0.86 g/cc to about 0.94 g/cc. The term linear low density polyethylene (LLDPE) is generally understood to include that group of ethylene/alpha-olefin copolymers which fall into the density range of about 0.915 g/cc to about 0.94 g/cc. Linear polyethylene in the density range from about 0.926 g/cc to about 0.94 g/cc is often referred to as linear medium density polyethylene (LMDPE). Lower density ethylene/alpha-olefin copolymers may be referred to as very low density polyethylene (VLDPE, typically used to refer to the ethylene/butene copolymers available from Union Carbide with a density ranging from about 0.88 g/cc to about 0.91 g/cc) and ultra-low density polyethylene (ULDPE, typically used to refer to the ethylene/octene copolymers supplied by Dow). Specific examples of useful, commercially available low density ethylene-1-octene copolymers include: Dowlex 2036A with a density in the range of 0.9330 g/cc to 0.9370 g/cc; Dowlex 2032PER with a density of 0.9240 g/cc to 9280 g/cc; Affinity PF1140 with a density of 0.895 g/cc to 0.898 g/cc; Affinity VP8770 with a density of 0.885 g/cc; Attane 4402 with a density of 0.912 g/cc; and Attane 4401 with a density of 0.912 g/cc. All of these copolymers are available from the Dow Chemical Co.

A variety of propylene copolymers are useful in the invention as the base layer. The propylene copolymers generally comprise copolymers of propylene and up to 10%, or even 20%, by weight of at least one other alpha olefin, such as ethylene, 1-butene, 1-pentene, etc. In one embodiment, the propylene copolymers are propylene-ethylene copolymers with ethylenic content from about 0.2% to about 10% by weight. Such copolymers are prepared by techniques well known to those skilled in the art, and these copolymers are available commercially from, for example, Union Carbide. A propylene-ethylene copolymer containing about 3.2% by weight of ethylene is available from Union Carbide under the designation D56D20. Another Union Carbide propylene-ethylene copolymer is D56D8, which contains 5.5% by weight of ethylene.

In another embodiment, the base layer comprises at least one thermoplastic copolymer or terpolymer derived from ethylene or propylene, and a functional monomer selected from the group consisting of alkyl acrylate, acrylic acid, alkyl acrylic acid, and combinations of two or more thereof. In one embodiment, the functional monomer is selected from alkyl acrylate, acrylic acid, alkyl acrylic acid, and combinations of two or more thereof. In one embodiment, the first polymer is characterized by the absence of ethylene vinyl acetate resins, and acid or acid/acrylate-modified ethylene vinyl acetate resins. The alkyl groups in the alkyl acrylates and the alkyl acrylic acids typically contain 1 to about 8 carbon atoms, and, in one embodiment, 1 to about 2 carbon atoms. The functional monomer(s) component of the copolymer or terpolymer ranges from about 1 to about 15 mole percent, and, in one embodiment, about 1 to about 10 mole percent of the copolymer or terpolymer molecule. Examples include: ethylene/methyl acrylate copolymers; ethylene/ethylacrylate copolymers; ethylene/butyl acrylate copolymers; ethylene/methacrylic acid copolymers; ethylene/acrylic acid copolymers; anhydride-modified low density polyethylenes; anhydride-modified linear low density polyethylene, and mixtures of two or more thereof.

Ethylene acid copolymers can also be used and are available from DuPont under the tradename Nucrel. These include Nucrel 0407, which has a methacrylic acid content of 4% by weight and a melting point of 109° C., and Nucrel 0910, which has a methacrylic acid content of 8.7% by weight and a melting point of 100° C. The ethylene/acrylic acid copolymers available from Dow Chemical, under the tradename Primacor, are also useful. These include Primacor 1430, which has an acrylic acid monomer content of 9.5% by weight, a melting point of about 97° C. and a $T_g$ of about −7.7° C. The ethylene/methyl acrylate copolymers available from Chevron, under the tradename EMAC, can be used. These include EMAC 2205, which has a methyl acrylate content of 20% by weight and a melting point of 83° C., and EMAC 2268, which has a methyl acrylate content of 24% by weight, a melting point of about 74° C. and a $T_g$ of about −40.6° C.

In one embodiment, the base layer comprises at least one polyester. Polyesters are prepared from various glycols (including ethylene glycol, propylene glycol, neopentyl glycol, etc.) or polyols (including glycerol, trimethylolpropane, pentaeythritol, etc.) and one or more aliphatic or aromatic carboxylic acids. Polyethylene terephthalate (PET), PETG (PET modified with cyclohexanedimethanol), and polybutylene terephthalate (PBT) are useful and are available from a variety of commercial sources, including Eastman. For example, Kodar 6763 is a PETG, available from Eastman Chemical. Another useful polyester from DuPont is Selar PT-8307, which is polyethylene terephthalate. Another useful polyester is polyethylene naphthenate.

In another embodiment, the base layer comprises at least one polystyrene (or styrenic polymer). Polystyrenes include homopolymers, as well as, copolymers of styrene and substituted styrene, such as alpha-methyl styrene. Examples of styrene copolymers and terpolymers include: acrylonitrile-butene-styrene (ABS); styrene-acrylonitrile copolymers (SAN); styrene butadiene (SB); styrene-maleic anhydride (SMA); styrene-methyl methacrylate (SMMA); etc. An example of a useful styrene copolymer is KR-10 from Phillip Petroleum Co. KR-10 is believed to be a copolymer of styrene with 1,3-butadiene.

In another embodiment, the base layer is composed of a polyacryl or polymethacryl resin. As used herein, a "polyacryl" includes polyacrylates, polyacrylics or polyacrylamides, and "polymethacryl" includes polymethacrylates, polymethacrylics or polymethacrylamides. These resins include those derived from acrylic acid, acrylate esters, acrylamide, methacrylic acid, methacrylate esters, and methacrylamide. The acrylate and methacrylate ester generally contain from 1 to about 30 carbon atoms in the pendant group, or from 1 to about 18 carbon atoms in the pendant group, or from 2 to about 12 carbon atoms in the pendant group.

Examples of commercial polyacryls and polymethacryls include Gelva® 2497 (commercially available from Monsanto Co., St. Louis, Mo.), Duraplus® 2 (commercially available from Rohm & Haas Co., Philadelphia, Pa.), Joncryl® 95 (commercially available from S. C. Johnson Polymer, Sturtevant, Wis.), SCX-1537 (S. C. Johnson Polymer), SCX-1959 (S. C. Johnson Polymer), SCX-1965 (S. C. Johnson Polymer), Joncryl® 530 (S. C. Johnson Polymer), Joncryl® 537 (S. C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Carboset® CR760 (commercially available from BFGoodrich, Cleveland, Ohio), Carboset® CR761 (BFGoodrich), Carboset® CR763 (BFGoodrich), Carboset® 765 (BFGoodrich), Carboset® 19X2 (BFGoodrich), Carbosete XL28 (BFGoodrich), Hycar 26084 (BFGoodrich), Hycar 26091 (BFGoodrich), Carbobond 26373 (BFGoodrich), Neocryl® A-601 (commercially available from Avecia Resins, Wilmington, Mass.), Neocryl® A-612 (Avecia Resins), Neocryl® A-6044 (Avecia Resins), Neocryl® A-622 (Avecia Resins), Neocryl® A-623 (Avecia Resins), Neocryle® A-634 (Avecia Resins), and Neocryl® A-640 (Avecia Resins).

Polycarbonates also are useful as the base layer of the present invention. Suitable polycarbonates are available from the Dow Chemical Co. (Calibre), G.E. Plastics (Lexan) and Bayer (Makrolon). Most commercial polycarbonates are obtained by the reaction of bisphenol A and carbonyl chloride in an interfacial process. Molecular weights of the typical commercial polycarbonates vary from about 22,000 to about 35,000, and the melt flow rates generally are in the range of from 4 to 22 g/10 min.

Coating Layer:

As noted above, the coating layer of the present invention is a combination of: (A) at least one adhesive resin and (B) at least one hydrophilic polymer, at least one surfactant or a combination of at least one hydrophilic polymer and at least one surfactant, with the proviso that when (B) is only a surfactant, then the coating layer contains less than about 40% by weight polyurethane. In one embodiment, the coating layer has a thickness of about 0.05 mil to about 10 mils, or from about 0.25 mil to about 7.5 mils, or from about 0.4 mil to about 5 mils.

In one embodiment, the compounds used to form the coating layer are chosen to yield a coating layer which promotes fluid transport. As is known in the art, the contact angle between the surface of a coated substrate and a droplet of water is an indicator of the hydrophilicity of the coating. The lower the contact angle, the better the hydrophilic properties of the coating. Static contact angles are measured at room temperature (about 25° C.) using a Rame-Hart goniometer Model A-100. The reported contact angle given in the examples below resulted from the average measured contact angle of four 4 μL water drops dripped onto a base layer coated with the desired coating layer to be tested.

In one embodiment, the coating layer of the present invention is formed to have a contact angle for water of about 22 degrees to about 50 degrees, or from about 25 degrees to about 45 degrees, or from about 28 degrees to about 40 degrees.

In one embodiment, the coating weight of the composition utilized for the coating layer is in the range of about 15 grams per square meter to about 60 grams per square meter, or from about 20 grams per square meter to about 55 grams per square meter, or from about 25 grams per square meter to about 50 grams per square meter.

In one embodiment, the coating layer is formed from a combination of at least one adhesive resin and at least one hydrophilic polymer. The coating layer generally contains about 30% to about 99%, or from 40% to about 90%, or from about 45% to about 85% by weight of one or more adhesive resins. The coating layer generally contains from about 1% to about 70%, or from 10% to about 60%, or from about 20% to about 55% by weight of one or more hydrophilic polymers.

In another embodiment, the coating layer contains from about 70% to about 95%, or from about 75% to about 90% by weight of one or more adhesive resins. In this embodiment, the coating layer contains from about 5% to about 30%, or from about 10% to about 25% by weight of one or more hydrophilic polymers.

In yet another embodiment, the coating layer is formed from a combination of at least one adhesive resin (which may be a hydrophobic polymer) and at least one surfactant. The coating layer contains about 70% to about 99.9%, or from about 80% to about 99%, or from about 85% to about 97%, or from about 90% to about 95% by weight of one or more adhesive resins. In this embodiment, the coating layer contains from about 0.1% to about 30%, or from about 1% to about 20%, or from about 3% to about 15%, or from about 5% to about 10% by weight of one or more surfactants.

In a further embodiment, the coating layer is formed from a combination of at least one adhesive resin, at least one hydrophilic polymer and at least one surfactant. In this embodiment, the coating layer contains from about 10% to about 90%, or from about 30% to about 70%, or from about 40% to about 60% by weight of one or more adhesive resins. The coating layer contains from about 10% to about 90%, or from about 30% to about 70%, or form about 40% to 60% by weight of one or more hydrophilic polymer. The coating layer contains from about 0.1% to about 10%, or from about 0.5% to about 7.5%, or from about 0.75% to about 5% by weight of one or more surfactants.

In yet another embodiment, the coating layer contains less than about 40% by weight polyurethane (which can act both as an adhesive resin and as a hydrophilic polymer), less than about 30% by weight polyurethane, less than about 10% by weight polyurethane, or even free of polyurethane (i.e., no polyurethane polymer is present). In one embodiment, the polyurethane is a water-dispersible polyurethane.

In one embodiment, the coating composition also includes at least one defoamer. The defoamers are present in an amount to prevent foaming of the coating composition. Typically, the defoamer is present in an amount from about 0.002% or from about 0.004% or from about 0.006% up to about 1%, or up to about 0.5%, or up to about 0.05% by weight of the coating composition. The defoamers may be a silicon based, hydrocarbon based, alcohol based or aqueous based defoamer. Combinations of defoamers may be used. Hydrocarbon-based, alcohol-based, silicone-based and water-based commercial products are available.

Hydrocarbon based defoamers generally have a hydrocarbon-based carrier and at least one defoaming additive. As used herein, the terms "hydrocarbon" or "hydrocarbon based" mean that the group being described has predominantly hydrocarbon character within the context of this invention. These include groups that are purely hydrocarbon in nature, that is, they contain only carbon and hydrogen. They may also include groups containing substituents or atoms which do not alter the predominantly hydrocarbon character of the group. Such substituents may include halo-, alkoxy-, nitro-, etc. These groups also may contain hetero atoms. Suitable hetero atoms will be apparent to those skilled in the art and include, for example, sulfur, nitrogen and oxygen. Therefore, while remaining predominantly hydrocarbon in character within the context of this invention, these groups may contain atoms other than carbon present in a chain or ring otherwise composed of carbon atoms.

In general, no more than about three non-hydrocarbon substituents or hetero atoms, and preferably no more than one, will be present for every 10 carbon atoms in the hydrocarbon or hydrocarbon based groups. Most preferably, the groups are purely hydrocarbon in nature, that is they are essentially free of atoms other than carbon and hydrogen.

The hydrocarbon carrier is generally present in an amount from about 5% to about 99%, or from about 35% to about 98%, or from about 50% to about 90% by weight of the defoamer. The hydrocarbon carrier is typically natural or synthetic oil. The oil is usually liquid at ambient temperatures. Natural oils include animal oils, vegetable oils, mineral lubricating oils, and solvent or acid treated mineral oils. Synthetic lubricating oils include hydrocarbon oils (polyalpha-olefins), halo-substituted hydrocarbon oils, alkylene oxide polymers, esters of dicarboxylic acids and polyols, esters of phosphorus-containing acids, polymeric tetrahydrofurans and silicon-based oils. Unrefined, refined, and rerefined oils, either natural or synthetic, may be used in the compositions of the present invention. In one embodiment, the hydrocarbon carrier is an alpha olefin or a polyalpha olefin (PAO). Exemplary hydrocarbon carriers, both alpha-olefins and PAOs, useful in a defoaming composition of the present invention include, without limitation, 1-hexene, 1-octene, 1-decene, 1-tetradecene, 1-heptene, 1-hexadecene, 1-octadecene, 1-nonene, 1-undecene, 1-tridecene, 1-pentadecene, 1-heptadecene, 1-nonadecene, isoparaffinic polyalphaolefin, polyalphaolefin polymers, and liquid polyethylene. Alpha-olefins and polyalpha-olefins are commercially available products from sources including Chevron and Henkel. Other hydrocarbons in stable liquid state characterized by no or a minimal number of chemical reactive groups which are useful as synthetic carrier fluids include polybutene and polyisobutylene.

The hydrocarbon-based defoamers also generally include a defoaming additive. The defoaming additive is generally present in an amount from about 1% to about 50%, or from about 3% to about 65%, or from about 5% to about 50% by weight of the defoamer. The defoaming additives are known to those in the art. Examples of these materials include hydrophobic silica, metal carboxylates, such as aluminum stearate; silicone oil, waxes, fatty (e.g., $C_{4-30}$) alcohols, fatty (e.g., $C_{4-30}$) acids, and ethoxylated fatty acids, polyalkylene glycols, such as polyethylene glycol, polypropylene glycol and polybutylene glycol, polysiloxanes, such as polyether modified polysiloxanes, polyalkylene glycol esters (including mono-, di- and triesters) of fatty acids, such as polyethylene glycol monooleate, polypropylene glycol distearate, and the like, polyoxypropylene-polyoxyethylene copolymers, alkylene bis fatty acid amides, such as ethylene-bis-stearamide and ethylene bis oleamide, polyalkylene polyamines, including polyethyleneamines, such as diethylenetriamine or triethylenetetramine and high density polymers. High density polymers are essentially linear polymer, i.e., lacking branches. Illustrative high density polymers include, without limitation, oxidized ethylene homopolymers, polypropylene homopolymers, ethylene homopolymers, polyethylene polymers and microcrystalline waxes formed of these components. The polyethylene polymers are generally water-insoluble, but are desirable, as they can be made into water-dispersible forms with suitable surfactants. Polyethylenes and other high density polymers are commercially available from sources including Petrolite Corporation and Astor Wax Corporation.

The defoamer compositions may further contain one or more surfactant compounds (non-ionic, anionic or cationic) to improve the efficiency of the defoamer compositions. Examples of suitable surfactants include those derived from polyethylene glycol, polypropylene glycol, polypropylene triol, butoxy polypropylene polyethylene glycol, dimethylpolysiloxane, alkoxylated dimethylpolysiloxane, and the like. Suitable surfactants are well known to those of skill in the art. See, for example, McCutcheon's *Emulsifiers and Detergents* (1992). The surfactants are generally present in an amount from about 0.1% to about 20%, from about 0.5% to about 10%, or from about 1% to about 5% of the defoamer.

The silicon-based defoamers use a silicon polymer as a carrier alone or with one or more of the above defoaming additives and/or surfactants. The silicon-based defoamers may also use some hydrocarbon based carriers but they are present in minor amounts. Typical silicon carriers are polydimethylsiloxanes. Useful polydimethylsiloxane oil is useful selected from those having a viscosity average between about 300 and about 500 cSt (25° C.) and an average molecular weight ($M_w$) between about 20,000 and about 40,000 with a molecular weight of about 28,000 to about 30,000 are useful. An example of a silicon based defoamer is a silicone/silica blend comprised of methylated silica and a dimethylsiloxane/silica reaction product in a weight ratio of 3.0% methylated silica to 27.0% dimethylsiloxane/silica reaction product and having a Brookfield RVT viscosity average between 1000 and 30,000 cps. These compounds are commercially available from Dow Corning as Dow Corning A and Dow Corning 3472, respectively. Silicone based defoaming agents are disclosed in U.S. Pat. Nos. 4,076,648; 5,380,464 and 5,523,019. The disclosures of which are incorporated herein by reference.

Examples of commercially available defoamers include Foamaster 1 1 1 (Henkel Corporation); Drewplus Defoamers such as L-140, L-191, Y-250, Y-281, L-418, L-435, L 464, and L-475 available from Ashland Chemical Co. Drew Industrial Division; Colloid 640 and 643 from Rhone-Poulenc Corp. Coatings and Construction Materials; Foam Blast 392 from Ross Chemical, Inc. Patco 841 from Patco Defoamers Additives of the American Ingredients Co. and FOAMEXTM™ 825 defoamer from Tego Chemie.

Adhesive Resin

As noted above, the coating layer of the present invention contains at least one adhesive resin. Adhesive resins suitable for use in the present invention include, but are not limited to, ethylene vinyl acetates, polyvinyl acetate ethylene emulsions, polyvinyl acetate acrylics (e.g., a polyvinyl acetate homopolymer emulsion), polyvinyl acetates (e.g., polyvinyl acetate homopolymer emulsion), vinyl acrylics or ethylene vinyl chloride.

In one embodiment, the glass transition temperature of the one or more adhesive resins of the present invention contained in the coating layer is at least about −20° C., or at least about −10° C., or at least about 0° C.

Examples of suitable ethylene vinyl acetate copolymers and terpolymers, such as those available under the tradename Airflex [e.g., Airflex 920 ($T_g$ −20° C., vinyl acetate/ethylene copolymer), Airflex 421 ($T_g$ 0° C., vinyl acetate/ethylene copolymer, self-crosslinking), Airflex 426 ($T_g$ 0° C., vinyl acetate/ethylene copolymer containing carboxyl groups), and Airflex 430 ($T_g$ 0° C., vinyl chloride/vinyl acetate/ethylene terpolymer) from Air Products and Chemicals Inc. (Allentown, Pa.)], and Allied Signal's A–C 5180 (vinyl acetate/ethylene copolymer with acid number of 180, available from Michelman Inc., Cincinnati, Ohio); and ethylene/acrylic acid copolymers, such as Michelman Emulsion 34040 (an aqueous dispersion of Allied Signal's ethylene/acrylic acid copolymer 5120) available from Michelman Inc. (Cincinnati, Ohio). In one embodiment, the ethylene vinyl acetate copolymers and terpolymers are vinyl acetate/ethylene copolymers, such as Airflex 920 or Airflex 300, available from Air Products.

Suitable ethylene vinyl chlorides, such as Airflex 4500, Airflex 4514 and Airflex 4530, can be used in the present invention and are available from Air Products and Chemicals, Inc. of Allentown, Pa.

Suitable polyvinyl acetate ethylene emulsion and polyvinyl acetate acrylic emulsion include those available from Air Products and Chemicals, Inc, Allentown, Pa., under the tradenames: Airflex 405, Airflex 410, Airflex 420, and Airflex 465; Flexbond 150, Flexbond 153, Flexbond 165 and Flexbond 825, respectively. Other suitable polyvinyl acetate acrylic emulsions are those having the tradenames Rovace 6930 and Rovace 3270, available from Rohm and Haas Company, Philadelphia, Pa. A suitable polyvinyl acetate homopolymer emulsion is available from Air Products and Chemicals, Inc., under the tradename Vinac 285.

Hydrophilic Polymer

As noted above, the coating layer of the present invention may contain at least one hydrophilic polymer. Hydrophilic polymers suitable for use in the present invention include, but are not limited to, cellulosic polymers, polyvinyl alcohol, polyvinyl pyrrolidone, dextran, nylons, polyamides, hydroxyethyl methacrylate, starches and gelatins.

Examples of suitable cellulosic polymers include, but are not limited to, hydroxyethyl cellulose, hydroxypropyl cellulose, methyl cellulose, ethyl cellulose, ethylhydroxyethyl cellulose, carboxymethyl cellulose or mixtures of two or more thereof.

Suitable polyvinyl alcohols are those having a degrees of hydrolysis of about 76 mole percent to almost 100 mole percent, or about 85 mole percent to about 99.5 mole percent, or even about 87 mole percent to about 99.3 mole percent. Examples of suitable polyvinyl alcohols are Celvol 502, Celvol 203, Celvol 205, Celvol 513, Celvol 523, Celvol 540, Celvol 418, Celvol 425, Celvol 310, Celvol 107, Celvol 305, Celvol 103, Celvol 125, Celvol 325, Celvol 165 and Celvol 350, all of which are available from Celanese Chemicals of Dallas, Tex.

As is known to those of skill in the art, as the degree of hydrolysis of a polyvinyl alcohol increases, its hydrophilicity tends to decrease relative to a polyvinyl alcohol with a lower degree of hydrolysis.

Surfactant

As noted above, the coating layer of the present invention may contain at least one surfactant. Surfactants suitable for use in the present invention include anionic surfactants, cationic surfactants, non-ionic surfactants or mixtures thereof. In one embodiment, the surfactants are those which provide improved fluid transport properties, even after desiccation.

Suitable anionic surfactants include, but are not limited to, aromatic or aliphatic anionic surfactants, normally a salt of an organic acid or ester, including carboxylates, sulfonates, sulfates, phosphonates, or combinations thereof. Suitable cationic surfactants include, but are not limited to, primary alkylamines (e.g., such as those sold under the tradename Armeen from Akzo Chemicals), tertiary amines (e.g., those sold under the tradename Ethomeen Armeen from Akzo Chemicals) or combinations thereof. Suitable nonionic surfactants include, but are not limited to, polyoxyethylene glycol ethers and esters, octylphenoxy polyethoxy ethanol surfactants, octyl phenol ethoxylate (such as those sold under the tradename Rexol 45 from Hart Chemicals) or combinations thereof.

Other functionalities may be present in the surfactant, particularly oxygen containing functionalities, such as ethers, esters, carbonyls, hydroxyl, or the like.

In one embodiment, the surfactant is at least one nonionic octylphenoxy polyethoxy ethanol surfactant sold under the tradenames Triton® X-100, Triton® X-102, Triton® X-114, Triton® X-165, Triton® X-305, Triton® X-405 (all available from Union Carbide). In another embodiment, the nonionic surfactant can be at least one sorbitan derivative, such as Tween 20 (polyoxyethylene (20) sorbitan monolaurate), Tween 40 (polyoxyethylene (20) sorbitan monopalmitate), Tween 60 (polyoxyethylene (20) sorbitan monstearate), or Tween 80 (polyoxyethylene (20) sorbitan monooleate) all available from ICI Americas Inc.

In one embodiment, the surfactant used in the coating layer of the present invention is at least one surfactant selected from N-octanoyl-N-methyl-D-glucamine (Mega 8), N-decanoyl-N-methyl-D-glucamine (Mega 10), cholic acid, hydroxypropyl ethylcellulose ("Methocel" 40–101 personal care grade), tetrapropylene diphenyloxide disulphonate sodium salt ("Dowfax 2A1"), capryloamphocarboxypropionate ("Mirarol J2M-SF"), polyoxyethylene 2 cetyl ether, polyethylene glycol, sodium lauryl sulfate, sodium lauryl sarcosinate, Surfynol 485 (2,4,7,9-tetramethyl-5-decyne-4,7-diol ethoxylate(30)), and mixtures thereof used either separately or in combination.

Adhesive Articles

Turning to FIG. 1, FIG. 1 depicts an adhesive article 100, according to one embodiment of the present invention. The adhesive article 100 of FIG. 1 includes a base layer 102 and a coating layer 104. The coating layer 104 is formed on one surface of the base layer 102 by any suitable technique. Suitable techniques include, but are not limited to, roll coating, spraying coating, casting, or application by gravure roll.

Figure 2:
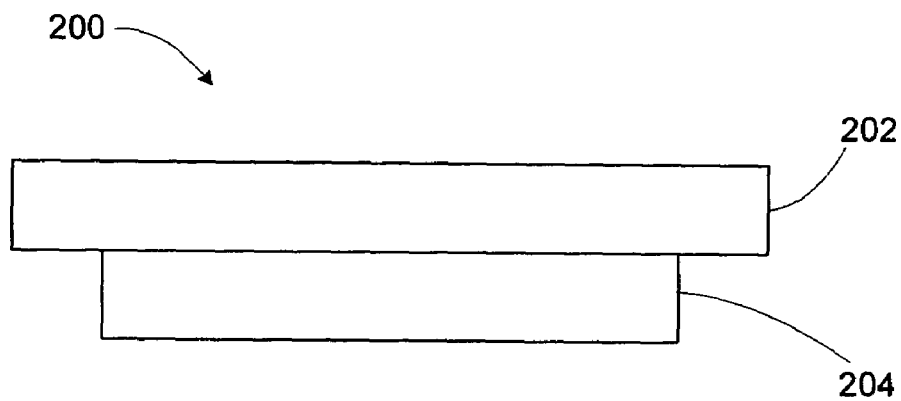
FIG. 2 is a cross-section view of an adhesive article, according to another embodiment of the present invention.

Turning to FIG. 2, FIG. 2 depicts an adhesive article 200, according to another embodiment of the present invention. The adhesive article 200 of FIG. 2 includes a base layer 202 and a coating layer 204. The coating layer 204 is formed on one surface of the base layer 202, as described above, by any suitable technique. In this embodiment, the coating layer does not completely cover the one surface of the base layer. The present invention is not limited to just the embodiment where there is a lip formed at either edge of the base layer. Depending upon the technique used to form the coating layer, a coating layer having practically any pattern can be formed on the base layer.

Methods for Forming the Adhesive Articles:

In one embodiment, the present invention relates to a method of making a hydrophilic adhesive article comprising the steps of: (A) providing a base layer having a first and second surface; and (B) forming at least one coating layer on at least one surface of a base layer, wherein the coating layer comprises at least one adhesive resin and at least one hydrophilic polymer; at least one adhesive resin (which can be a hydrophobic polymer) and at least one surfactant; or at least one adhesive resin, at least one hydrophilic polymer and at least one surfactant.

In another embodiment, the present invention relates to a method of making at least one area more hydrophilic, which includes the steps of: (A) forming an adhesive article comprising a base layer having a first and second surface and at least one coating layer on at least one surface of a base layer, the coating layer comprising: (i) at least one adhesive resin; and (ii) at least one hydrophilic polymer, and (B) placing the at least one adhesive article in a suitable location to increase the hydrophilic properties in the surrounding area.

After the coating layer has been formed on the base layer, the adhesive article so produced can be optionally subjected to a desiccation step. The desiccation step can be conducted at room temperature (approximately 25° C.) or at an elevated temperature. If the optional desiccation step is conducted at an elevated temperature, such a temperature can be in the range of about 30° C. to about 170° C., or at a temperature of 50° C. to about 150° C., or at a temperature of about 60° C. to about 130° C.

The optional desiccation step can be conducted for any suitable period of time. In one embodiment, the desiccation step is conducted for a period of about 5 minutes to about 120 minutes, or from about 10 minutes to about 90 minutes, or from about 15 minutes to about 60 minutes. In another embodiment, the optional desiccation step of the present invention is conducted at a suitable temperature, as noted above, for a period of about 1 day to about 21 days, or from about 2 days to about 18 days, or from about 3 days to about 14 days.

Ideally, the above-mentioned desiccation step should remove substantially all of any liquids which may be contained in the coating layer and/or the base layer. In one embodiment, the amount of retained liquid remaining in the coating layer and/or the base layer after the desiccation is less than about 10% by weight, or even less than about 5% by weight, or less than about 1% by weight.

EXAMPLES

The following examples, 1 to 25, are prepared by mixing the stated components in the weight amounts shown bellow and coated onto 5 mil thick PET films (size 12 inches by 15 inches) by coating to a thickness of 2.5 mils.

Examples 1–7 illustrate the coating layers prepared from the combination of an adhesive resin and a hydrophilic polymer.

|  | EVA | PVOH |
|---|---|---|
| Example 1 | 90% | 10% |
| Example 2 | 80% | 20% |
| Example 3 | 70% | 30% |
| Example 4 | 60% | 40% |
| Example 5 | 50% | 50% |
| Example 6 | 40% | 60% |
| Example 7 | 30% | 17% |

Examples 8 to 12 illustrate coating layers prepared from the combination of an adhesive resins and a surfactant.

|  | EVA | Sodium Lauryl Sulfate |
|---|---|---|
| Example 8 | 97% | 3% |
| Example 9 | 95% | 5% |
| Example 10 | 90% | 10% |
| Example 11 | 80% | 20% |
| Example 12 | 70% | 30% |

Example 13 to 25 illustrate the coating layers prepared from the adhesive resin and a hydrophilic, a surfactant, or a combination of a hydrophilic polymer and a surfactant. Samples 13, 18, 19, 21 and 22 are coating compositions containing a combination of an adhesive resin and a surfactant. Samples 15 16, 23, 24 and 25 are coating compositions containing a combination of an adhesive resin, a hydrophilic polymer (e.g., PVOH) and a surfactant (e.g., sodium lauryl sulfate). Samples 14, 17 and 20 are coating compositions containing an adhesive resin and a combination of a hydrophilic polymer and a surfactant.

The samples are then subjected to different atmospheric conditions (e.g., stored at room temperature for 7 days or 16 days, subjected to desiccation for 3 days, 7 days or 16 days, all at 60° C. to simulate to the conditions of extended storage prior to use). The results of the flow of water across these films and the contact angles of water droplets (as measured in accordance with the test discussed above) are detailed in Table 1.

For the flow test, 6 micro liters of water is deposited on a coated (or an uncoated) film and the speed of the flow of the water across the film observed. In the results detailed in Table 1, the following numerical values are used to denote the speed of the water flow across the sample films: 0=no flow; 1=very slow flow; 2=slow flow; 3=fair flow; 4=good flow; and 5=very good flow. Where two numerical values are given, the flow observed lies somewhere between two numerical flow values. Depending upon which numerical value is listed first, the flow is observed to be closer to that numerical flow value than the flow value listed second.

Additionally, it was observed that regardless of whether the water was allowed to flow in the machine direction or cross direction of the base film, the flow values observed were the same for both the coated and uncoated samples.

TABLE 1

| Sample | Coating Formulation | | | Initial Flow (1) | 3 Day Desiccated (2) | 7 Day at RT (3) | 7 Day Desiccated (4) | 16 Day at RT (5) | 16 Day Desiccated (6) | Water Contact Angle | |
|---|---|---|---|---|---|---|---|---|---|---|---|
| | EVA | PVOH | Surfactant | | | | | | | RT | Aged (7) |
| 13 | 99 | 0 | 1 | 5/4 | 3 | 1/2 | 2/3 | 2 | 3 | 24.5 | 30.3 |
| 14 | 0 | 99 | 1 | 5 | 3/4 | 4/5 | 4 | 3/4 | 3 | 28.0 | 33.7 |
| 15 | 49.5 | 49.5 | 1 | 5 | 4/5 | 4 | 4 | 3/4 | 4 | 32.3 | 34.2 |
| 16 | 47.5 | 47.5 | 5 | 4 | 4 | 3 | 3 | 3 | 3/4 | 19.8 | 31.3 |
| 17 | 0 | 95 | 5 | 3 | 2/3 | 2/3 | ¾ | 3/4 | 3 | 18.7 | 25.3 |
| 18 | 95 | 0 | 5 | 3 | 2 | 3 | 2 | 2 | 3 | 22.8 | 24.7 |
| 19 | 99 | 0 | 1 | 4 | 3 | 2/3 | 2/3 | 2/3 | 3 | 26.5 | 41.5 |
| 20 | 0 | 97 | 3 | 3 | 3 | 2/3 | ¾ | 3 | 4 | 27.2 | 26.2 |
| 21 | 97 | 0 | 3 | 2 | 2 | 2/3 | 2 | 2/3 | 2/3 | 17.0 | 32.0 |
| 22 | 95 | 0 | 5 | 2 | 1 | 2 | ¾ | 2 | 3 | 22.2 | 31.5 |
| 23 | 49.5 | 49.5 | 1 | 4/5 | 2/3 | 3/4 | 4 | 2/3 | 3 | 29.7 | 36.8 |
| 24 | 48.5 | 48.5 | 3 | 3 | 4 | 3/4 | ¾ | 2 | 2 | 23.7 | 32.2 |
| 25 | 75 | 25 | 5 | 2 | 3/4 | 2 | ¾ | 2 | 2 | 14.8 | 25.0 |

EVA is ethylene vinyl acetate (Airflex 300 from Air Products;
PVOH is polyvinyl alcohol (Celvol 205 from Celanese));
and the surfactant was sodium lauryl sulfate.
(1) This value is the value generated by a test conducted at room temperature after the production of the coated samples are completed.
(2) This value is the value generated by a test conducted on a sample at room temperature after the coated sample had been subjected to desiccation for 3 days at 60° C.
(3) This value is the value generated by a test conducted on a test sample that was stored at room temperature for 7 days.
(4) This value is the value generated by a test conducted on a sample at room temperature after the coated sample had been subjected to desiccation for 7 days at 60° C.
(5) This value is the value generated by a test conducted on a test sample that was stored at room temperature for 16 days.
(6) This value is the value generated by a test conducted on a sample at room temperature after the coated sample had been subjected to desiccation for 16 days at 60° C.
(7) These samples were then coated and subjected to desiccation at 60° C. and then tested.

Examples 26–34 illustrate coating compositions containing a defoamer.

| Sample | EVA[1] | EVA[2] | PVOH | Surfactant | Defoamer | Water |
|---|---|---|---|---|---|---|
| 26 | 95 | 0 | 0 | 1 | 0.1 | 5 |
| 27 | 95 | 0 | 0 | 1 | 0.1 | 5 |
| 28 | 94 | 0 | 5 | 1 | 0.1 | 5.5 |
| 29 | 94 | 0 | 5 | 0 | 0.1 | 5.5 |
| 30 | 89 | 0 | 10 | 1 | 0.1 | 5.5 |
| 31 | 0 | 89 | 10 | 1 | 0.1 | 15 |
| 32 | 0 | 89 | 10 | 0 | 0.1 | 15 |
| 33 | 0 | 85 | 15 | 1 | 0.1 | 15 |
| 34 | 0 | 92 | 12 | 1 | 0.1 | 15 |

[1]EVA is ethylene vinyl acetate (Airflex 465 from Air Products)
[2]EVA is ethylene vinyl acetate (Airflex 920 from Air Products)
3) PVOH is polyvinyl alcohol (Celvol 205 from Celanese)
4) Surfactant is sodium lauryl sulfate
5) Defoamer is Drewplus Y-250

Each of the above formulations is compounded and filtered through a 100 micron bag. The coating composition is coated on to 5 mil polyester (PET) film. Examples 26–30 are coated at a coat weight of 37 grams per square meter (gsm) and cured at an oven temperature from 180–215° F. Examples 31–34 are coated at a coat weight of 30 gsm and cured at an oven temperature from 165–190° F.

Lidded Articles

As is noted above, an adhesive article according to the present invention can be used to increase the hydrophilic (or even the hydrophobic) nature of one or more areas on a device which contain at least one fluid transport structure (i.e., structures and/or areas involved in the transport of one or more fluids from one point on a device to another point on a device).

At a minimum, devices which include one or more fluid transport structures have the following minimum components. A substrate (e.g., a base layer) which is formed from a suitable material (e.g., polycarbonate, polyesters, polyolefins, glass, etc.) and one or more fluid transport structures. As an example, fluid transport structures can be one or more of the following: a groove, a depression of any shape or a channel which permits fluid flow or movement. The one or more fluid transport structures can be provided by embossing the desired shape, groove or channel into a substrate using known embossing techniques.

Alternatively, the one or more fluid transport structures can be produced by placing one or more additional layers onto or on top of the substrate layer. The additional layers include, but are not limited to, some or all of the following: ink layers, conductive material layers (e.g., conductive metal layers), spacer layers (which can be formed from similar or different materials than the substrate layer), or adhesive layers.

In light of the above structures, an adhesive article according to the present invention can be placed on top of or next to the one or more fluid transport structures. If an adhesive article according to the present invention is placed next to one or more fluid transport structures, an adhesive article should be within about 20 microns to about 4000 microns of the area surrounding the one or more fluid transport structures where increased hydrophilicity (or even hydrophobicity) is desired. In another embodiment, at least one adhesive article is located within about 50 microns to about 2000 microns, or even within about 100 microns to about 1000 microns of any area where increased hydrophilicity (or even hydrophobicity) is desired.

The adhesive article of the present invention, which is being used to increase the hydrophilic or hydrophobic nature of the one or more fluid transport structures, can be applied by heat sealing. Heat sealing techniques are known in the art and are discussed briefly below.

Figure 3:
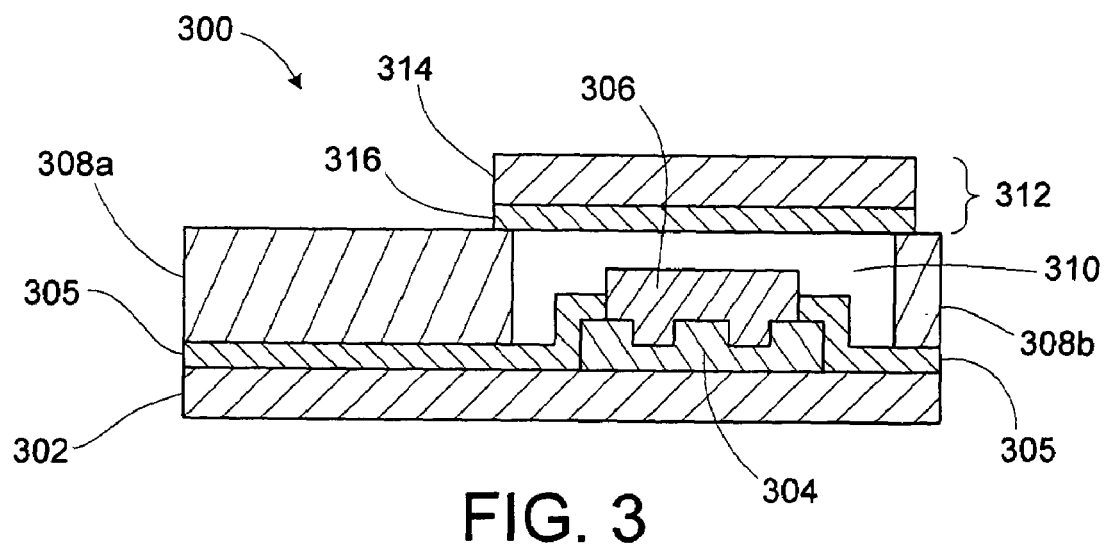
FIG. 3 is a cross-section view of one adhesive article according to one embodiment of the present invention, as it may be utilized as a cover for a biosensor device.

FIG. 3 depicts a biosensor with a cover which is provided by the adhesive article of the present invention. The biosensor 300 of FIG. 3 includes an insulating base plate 302 formed of, for example, polycarbonate or polyethylene terephthalate, an electrical conductive pattern 304 which can include, for example, an electrode for measurement and a counter electrode, or an electrode for measurement, a counter electrode and a reference electrode. Such electrode systems are known in the art and, as such, are generally shown as reference numeral 304 without depicting all of the subcomponents thereof. Next, an insulating layer 305 is formed over at least a portion of the base plate 302 and, in some circumstances, the electrode system 304. A reaction layer 306 is formed over at least a portion of the electrode system 304. Spacers 308a and 308b are adhered to the insulating layer 305 by any suitable technique as is known in the art. Although not depicted in FIG. 3, spacer 308b may be two or more individual pieces so as to allow for one or more openings to be formed in the width of the biosensor of FIG. 3. This opening, if present permits the entry of a sample fluid into a sample space 310, which is formed after the application of a cover 312. Alternatively, an opening to allow for the entry of a sample into sample space 310 may be formed elsewhere on the biosensor, as is known in the art in one embodiment, the sample space formed by the application of cover 312 to the top of sample space 310 is from about 10 microns to about 1000 microns in height, or from about 25 microns to about 500 microns in height, or even from about 50 microns to about 300 microns in height.

Cover 312 is an adhesive article in accordance with an embodiment of the present invention having a base layer 314 and a coating layer 316 as described above. Cover 312 can be applied so as to cover an area slightly larger than the top opening of sample space 310 or can be formed so as to cover all of biosensor 300 (not shown). In one embodiment, cover 312 can be formed so as to have at least one opening therein to permit the entry of a sample into a sample space located below cover 312, the discharge of gas trapped in sample space 310 to an area outside the biosensor 300 and/or both.

As would be apparent to one of skill in the art, in the production of biosensors, more than one biosensor could be present in a master sheet of biosensors and an adhesive article in accordance with the present invention could be applied individually to cover the top of each sample space present in each biosensor or an adhesive article in accordance with the present invention could be applied as a single sheet in order to cover all of the sample spaces present in the biosensors located on the production sheet. The application of a single master cover is advantageous because it simplifies the simultaneous production of a large number of biosensors by permitting a cover to be applied to all of the biosensors present in a production sheet in one step.

Alternatively, various other methods for covering more than one biosensor on a production sheet, but not all, could be used. For example, strips of adhesive articles in accordance with the present invention could be used to cover rows (or columns) of biosensors on a production sheet thereof. This option saves production steps versus covering each sensor individually and eliminates waste versus covering the complete production sheet.

It should be noted that the use of an adhesive article in accordance with the present invention as a cover or a portion of a biosensor is not limited to the biosensor depicted in FIG. 3. Rather, an adhesive article in accordance with the present invention can be used in any biosensor, regardless of the sensor's layout, in which a layer is needed to increase the hydrophilicity (or even hydrophobicity) of one or more areas or spaces.

Generally, when the adhesive article of the present is utilized as a biosensor cover, the adhesive article is applied utilizing a heat seal technique. That is, an adhesive article in accordance with the present invention can be activated for fusing to the base at a temperature sufficiently low to avoid damage to the reagents in the reagent layer while forming a good bond with one or more underlying layers (e.g., insulating layer 306), while at the same time yielding a long lasting biosensor having a good shelf life. Given the nature of the coating layer contained in the adhesive article, the coating can also increase the hydrophilic nature (or in some cases, the hydrophobic nature) of the interior of at least the topside of the sample space 310.

The adhesive article may be used in biosensors, bandages, medical or chemical testing devices, etc. The adhesive article should possess fair to good adhesion to UV inks so that the adhesive article can be easily applied as desired. Depending upon the specific use, long term stability or strong adhesion may not be required.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. An article for fluid transport comprising:
   a substrate having at least one fluid transport structure;
   at least one adhesive article, the adhesive article comprising:
   a base layer having a first and second surface; and
   at least one coating layer on at least one surface of a base layer, the coating layer comprising: (A) at least one adhesive resin and (B) at least one hydrophilic polymer, at least one surfactant or a combination of at least one hydrophilic polymer and at least one surfactant, with the proviso that when (B) is only a surfactant, then the coating layer contains less than about 40% by weight polyurethane; and wherein the hydrophilic polymer is selected from cellulosic polymers, polyvinyl alcohol, polyvinyl pyrrolidone, dextran, nylons, polyamides, hydroxyethyl methacrylate, starches and gelatins: and
   wherein the at least one adhesive article is heat sealed to the substrate and covers the at least one fluid transport structure and the coating layer is positioned to contact fluid of the fluid transport structure.

2. The article of claim 1, wherein the coating layer comprises at least one adhesive resin and at least one hydrophilic polymer.

3. The article of claim 2, wherein the coating layer comprises from about 30% to about 99% by weight adhesive resin and from about 1% to about 70% by weight hydrophilic polymer.

4. The article of claim 1, wherein the coating layer comprises at least one adhesive resin and at least one surfactant.

5. The article of claim 4, wherein the coating layer comprises from about 70% to about 99.9% by weight adhesive resin and from about 0.1% to about 30% by weight surfactant.

6. The article of claim 1, wherein the coating layer comprises at least one adhesive resin, at least one hydrophilic polymer and at least one surfactant.

7. The article of claim 1, wherein the coating layer comprises from about 10% to about 90% by weight adhesive resin, from about 10% to about 90% by weight hydrophilic polymer, and from about 0.1% to about 10% by weight surfactant.

8. A biosensor comprising:
a base plate having an electrode system;
a sample space formed on the base plate, the sample space being formed in such a manner as to enable the input of a sample;
a reaction layer located in the sample space; and
a cover for covering the top portion of the sample space, the cover being formed from an adhesive article, wherein the adhesive article comprises:
a base layer having a first and second surface; and
at least one coating layer on at least one surface of a base layer, the coating layer comprising: (A) at least one adhesive resin and (B) at least one hydrophilic polymer, at least one surfactant or a combination of at least one hydrophilic polymer and at least one surfactant, with the proviso that when (B) is only a surfactant, then the coating layer contains less than about 40% by weight polyurethane.

9. The biosensor of claim 8, wherein the coating layer comprises at least one adhesive resin and at least one hydrophilic polymer.

10. The biosensor of claim 9, wherein the coating layer comprises from about 30% to about 99% by weight adhesive resin and from about 1% to about 70% by weight hydrophilic polymer.

11. The biosensor of claim 8, wherein the coating layer comprises at least one adhesive resin and at least one surfactant.

12. The biosensor of claim 11, wherein the coating layer comprises from about 70% to about 99.9% by weight adhesive resin and from about 0.1% to about 30% by weight surfactant.

13. The biosensor of claim 8, wherein the coating layer comprises at least one adhesive resin, at least one hydrophilic polymer and at least one surfactant.

14. The biosensor of claim 13, wherein the coating layer comprises from about 10% to about 90% by weight adhesive resin, from about 10% to about 90% by weight hydrophilic polymer, and from about 0.1% to about 10% by weight surfactant.

15. The biosensor of claim 8 further comprising an insulating layer formed over at least a portion of the base plate.

16. The biosensor of claim 8 further comprising an insulating layer formed over at least a portion of the base plate and a portion of the electrode system.

17. The biosensor of claim 8 wherein the sample space is formed by the cover and at least one spacer between the cover and the substrate.

18. The biosensor of claim 17 wherein the at least one spacer comprises two or more individual pieces.

19. The article of claim 1 wherein the adhesive article is positioned to form a space within the fluid transport structure.

20. The article of claim 1 wherein the adhesive article is positioned on at least one spacer to form a space within the fluid transport structure.

21. The article of claim 20 wherein the space is formed by the adhesive article and the at least one spacer between the adhesive article and the substrate.

22. The article of claim 20 wherein the at least one spacer comprises two or more individual pieces.

* * * * *